United States Patent
Foote

(10) Patent No.: US 9,382,623 B2
(45) Date of Patent: Jul. 5, 2016

(54) APPARATUS AND METHOD FOR INTRALUMINAL POLYMER DEPOSITION

(71) Applicant: Nordson Corporation, Westlake, OH (US)

(72) Inventor: David K. Foote, San Jose, CA (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 14/304,199

(22) Filed: Jun. 13, 2014

(65) Prior Publication Data

US 2015/0361558 A1    Dec. 17, 2015

(51) Int. Cl.
| | |
|---|---|
| *H05H 1/02* | (2006.01) |
| *H05H 1/24* | (2006.01) |
| *C23C 16/509* | (2006.01) |
| *C23C 16/515* | (2006.01) |
| *A61L 31/08* | (2006.01) |
| *B05D 1/00* | (2006.01) |
| *C23C 16/04* | (2006.01) |
| *B05D 7/22* | (2006.01) |

(52) U.S. Cl.
CPC ............. *C23C 16/5093* (2013.01); *A61L 31/08* (2013.01); *B05D 1/62* (2013.01); *C23C 16/045* (2013.01); *C23C 16/509* (2013.01); *C23C 16/515* (2013.01)

(58) Field of Classification Search
CPC .. B29C 59/142; C23C 16/045; C23C 16/505; C23C 16/54
USPC .................................. 427/574, 569, 230, 238
See application file for complete search history.

(56) References Cited

U.S. PATENT DOCUMENTS

| | | | | |
|---|---|---|---|---|
| 4,261,806 A | * | 4/1981 | Asai et al. ...................... 204/165 |
| 4,473,596 A | * | 9/1984 | Beerwald et al. ................ 427/10 |
| 4,488,954 A | * | 12/1984 | Hatada et al. .................. 204/169 |
| 4,692,347 A | * | 9/1987 | Yasuda ........................... 427/491 |
| 5,030,476 A | * | 7/1991 | Okamura et al. .............. 427/575 |
| 5,198,033 A | * | 3/1993 | Kelley et al. ................... 118/718 |
| 5,593,550 A | * | 1/1997 | Stewart et al. ................. 204/165 |
| 6,101,973 A | * | 8/2000 | Stewart et al. .......... 118/723 ER |
| 7,300,684 B2 | * | 11/2007 | Boardman ............. C23C 16/045 118/663 |
| 2009/0099512 A1 | * | 4/2009 | DiGregorio et al. ............ 604/90 |
| 2009/0311443 A1 | * | 12/2009 | Boardman ............. C23C 16/045 427/569 |
| 2010/0028572 A1 | * | 2/2010 | Kobayashi et al. ........... 428/34.1 |
| 2010/0298738 A1 | * | 11/2010 | Felts et al. ..................... 600/576 |
| 2012/0231177 A1 | * | 9/2012 | Wei et al. ....................... 427/523 |

OTHER PUBLICATIONS

Nordson March "AP-1000 Robust Pasma Treatment System" Product Brochure Reformatted Jun. 2013.
March, A Nordson Company, "AP-1000 Plasma System", Product Brochure Jun. 2008.

* cited by examiner

*Primary Examiner* — Kelly M Gambetta
(74) *Attorney, Agent, or Firm* — Baker & Hostetler LLP

(57) ABSTRACT

Methods and apparatus for applying a coating to an interior surface surrounding a passage of an article. A plasma is generated from a process gas inside the passage of the article, and the coating is deposited from the plasma on the interior surface. The article may optionally be placed inside of a passage of a conductive conduit. Either the article or the conductive conduit is coupled with a radio-frequency generator for generating the plasma inside the passage of the article.

10 Claims, 6 Drawing Sheets

APPARATUS AND METHOD FOR INTRALUMINAL POLYMER DEPOSITION

BACKGROUND

The invention relates generally to plasma processing and, in particular, to methods and apparatus for coating a surface with a film.

Silicone rubber materials are used in a wide variety of applications including high temperature seals and o-rings, handle grips, electrical insulators, implantable devices, etc. Silicone rubbers are very tacky which can cause problems in applications where low surface friction is required, particularly on interior passage surfaces when threading an object through a passage.

Therefore, there is a need for methods and apparatus to reduce the coefficient of dynamic friction between the interior surface surrounding a passage and an object that is in contact with the interior surface.

SUMMARY

In one embodiment, a method is provided for applying a coating to an interior surface surrounding a passage in an article. The method includes generating a plasma from a process gas inside the passage of the article, and depositing the coating from the plasma on the interior surface.

In another embodiment, an apparatus is provided for applying a coating to an interior surface of a passage of an article. The apparatus includes a process chamber, a radio-frequency generator, and a conductive conduit having a passage configured to receive the article. The conductive conduit is positioned inside of the process chamber, and the conductive conduit is coupled with the radio-frequency generator for receiving power to generate a plasma inside of the passage in the article when the article is received in the passage of the conductive conduit.

BRIEF DESCRIPTION OF THE SEVERAL VIEWS OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

Figure 1:
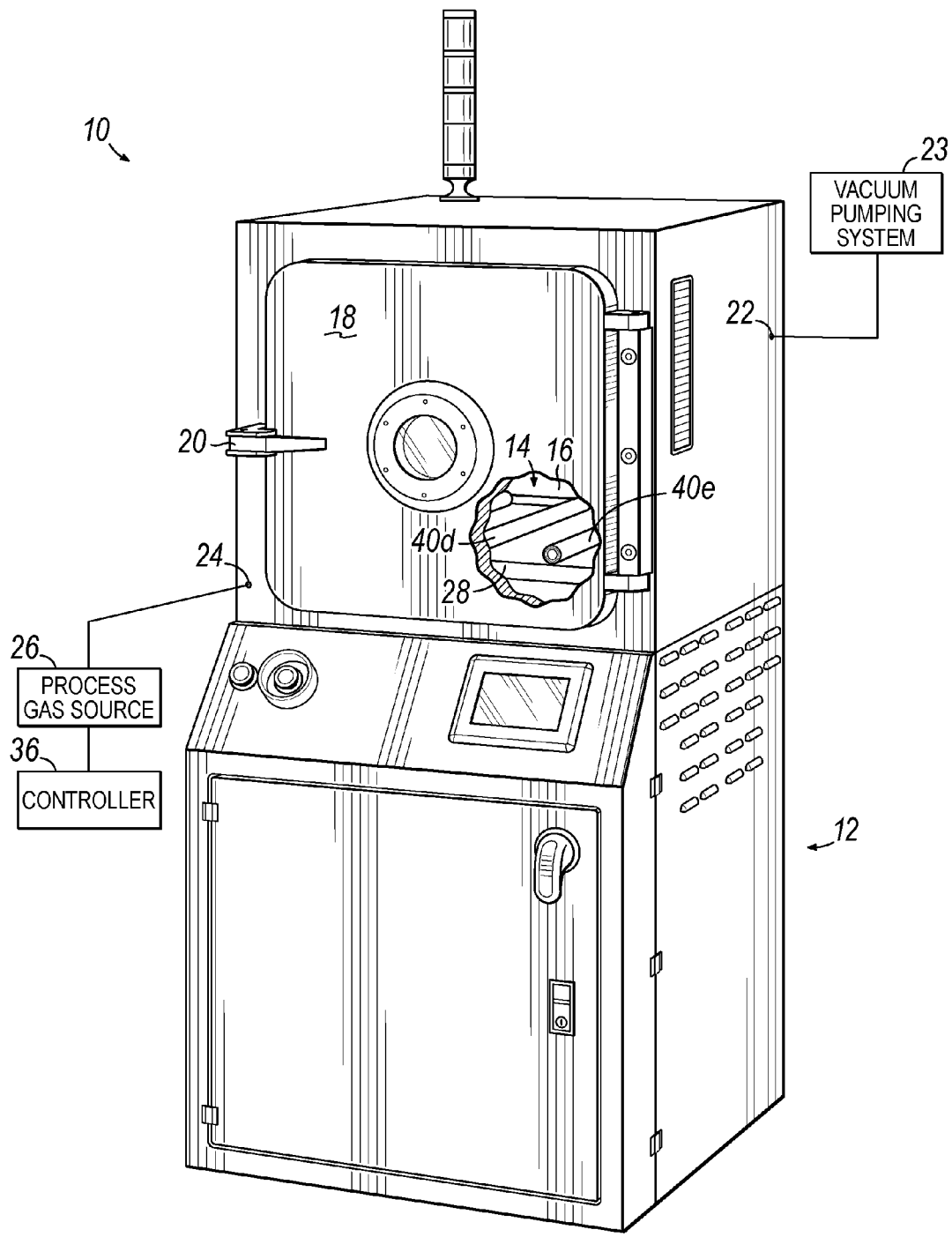
FIG. 1 is a front perspective view of a plasma treatment system.
Figure 2:
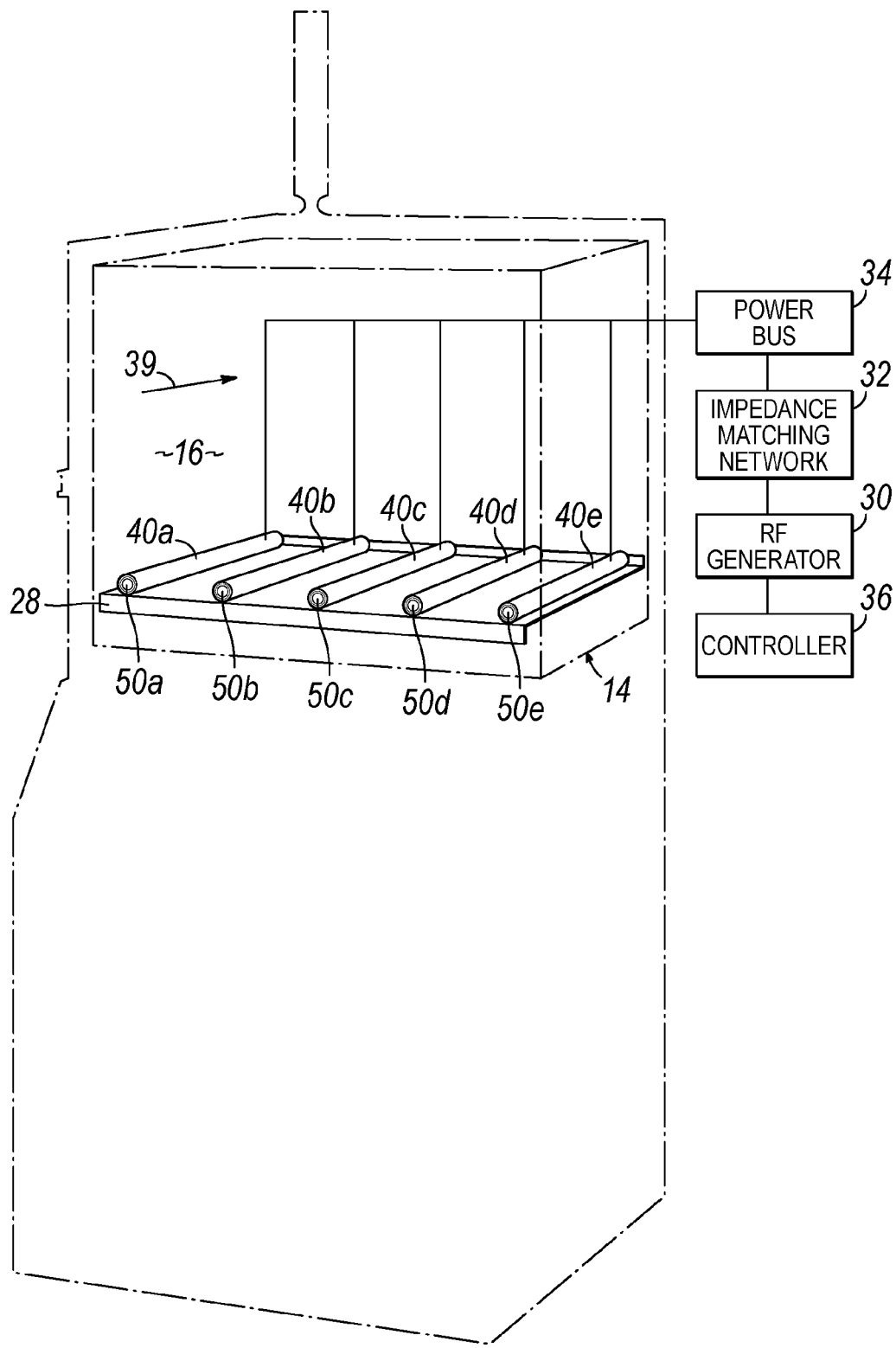
FIG. 2 is a view showing the evacuable space of the process chamber of the plasma treatment system and the conduits and associated tubes disposed inside the evacuable space in accordance with an embodiment of the invention.

With reference to FIGS. 1 and 2, a plasma treatment system 10 includes a cabinet 12, a reaction or process chamber 14 associated with the cabinet 12, and an evacuable space 16 surrounded by walls of the process chamber 14. The evacuable space 16 is accessed through an access opening defined in the walls of the process chamber 14. A chamber door 18 can be opened and closed to provide access through the access opening to the evacuable space 16. In its closed condition, the chamber door 18 supplies a fluid-tight seal that isolates the evacuable space 16 from the surrounding ambient environment of the process chamber. The chamber door 18, which may have a hinged attachment, carries a latch 20 that engages a portion of the process chamber 14 when the chamber door 18 is in the closed position. The latch 20 is used to secure the chamber door 18 for sealing the process chamber 14 from the ambient environment. The process chamber 14 is formed of an electrically conductive material suitable for high-vacuum applications, such as an aluminum alloy or stainless steel, and may be coupled with electrical ground.

The evacuable space 16 defined inside the process chamber 14 is evacuated through a pump port 22 in the process chamber 14 by a vacuum pumping system 23. The vacuum pumping system 23, which may be located inside the cabinet 12 or on the floor adjacent to the cabinet 12, is connected with the pump port 22. The vacuum pumping system 23 may comprise one or more vacuum pumps having a construction and operation recognized by a person of ordinary skill in the art of vacuum technology. For example, the vacuum pumping system 23 may include a rotary vane pump and a roots blower that cooperate to establish and maintain a vacuum pressure within the process chamber 14 that is in the mTorr range. The vacuum pumping system 23 is used to evacuate atmospheric gases from the evacuable space 16 each time that the evacuable space 16 is vented and, in addition, to provide a continuous directional flow of processing gas from, for example, one or more gas ports 24 near the front of the process chamber 14 to the pump port 22 located near the rear of the process chamber 14. The gas ports 24 are coupled by a gas line with a process gas source 26.

The plasma treatment system 10 includes at least one shelf 28 located inside the process chamber 14 and a plasma excitation source in the representative form of a radio-frequency (RF) generator 30. The output of the RF generator 30 may be coupled through an impedance matching network 32 with a power bus 34, which in turn includes conductive members that are coupled with conductive conduits 40a-40e inside the evacuable space 16. The walls of the process chamber 14 may function as an unpowered, grounded counterelectrode. The RF generator 30 may operate at a frequency of, for example, 13.56 MHz. The power supplied by the RF generator 30 may, for example, range from about 100 watts to about 300 watts at 13.56 MHz. The RF generator 30 may be configured to operate to deliver power in a pulsed manner and, specifically, with pulsing parameters such as a pulsing frequency (Hz) and a duty cycle (% on time). For example, the pulsing frequency may be adjusted within a range of 1 Hz to 10,000 Hz and the duty cycle may be adjusted in a range of 1% to 99% to define different combinations of pulsing parameters.

A controller 36 for the plasma treatment system 10 may be implemented on one or more computing devices or systems (collectively referred to herein as a computer). The controller 36 may include at least one processor, a memory, a mass storage memory device, an input/output (I/O) interface, and a Human Machine Interface (HMI). The computer may also be operatively coupled to one or more external resources via a network and/or the I/O interface.

The processor of the controller 36 may operate under the control of an operating system that resides in the memory. The operating system may manage computing resources so that computer program code embodied as one or more computer software applications, such as a computer software application resident in the memory, may have its instructions executed by the processor. One or more data structures may also reside in the memory, and may be used by the processor, operating system, or application of the controller 36 to store or manipulate data, such as data providing recipes for the operation of the plasma treatment system 10 to perform depositions.

The I/O interface of the controller 36 may provide a machine interface that operatively couples the processor to the hardware (e.g., the vacuum pumping system 23, the process gas source 26, the RF generator 30) used by the plasma treatment system 10 to perform the plasma depositions described herein. The application may thereby work cooperatively with the hardware by communications over the I/O interface to provide the various features, functions, or processes comprising embodiments of the invention.

The HMI of the controller 36 may be operatively coupled to the processor in a known manner to allow a user to interact directly with the computer. The HMI may include video or alphanumeric displays, a touch screen, a speaker, and any other suitable audio and visual indicators capable of providing data to the user. The HMI may also include input devices and controls such as an alphanumeric keyboard, a pointing device, keypads, pushbuttons, control knobs, microphones, etc., capable of accepting commands or input from the user and transmitting the entered input to the processor.

A database may reside on the mass storage memory device of the controller 36, and may be used to collect and organize data used by the plasma treatment system 10, such as data providing recipes for procedures to operate the plasma treatment system 10. The database may include data and supporting data structures that store and organize the data, and a database management system in the form of a computer software application used to access the information or data stored in records of the database in response to the initiation of a procedure to perform a plasma deposition.

A plurality of conductive conduits 40a-40e are arranged inside of the process chamber 14. The conductive conduits 40a-40e comprise reusable and recyclable components that are used to batch process successive sets of articles in the representative form of tubings or tubes 50a-50e by forming a polymerized coating or film on an internal or interior surface 53 of an internal passage having the representative form of a lumen 54 in each of the tubes 50a-50e.

The process gas source 26 may include one or more mass flow controllers configured to control the flow of process gas to the evacuable space 16 inside process chamber 14. The process gas source 26 may regulate both the gas pressure and the gas mixture in the evacuable space 16. The process gas source 26 may supply a process gas comprising an inert gas and a precursor monomer in the form of a vapor or gas that are each present in the evacuable space 16 at a total process pressure sufficient to sustain a hollow cathode plasma within the passages 44 of the conductive conduits 40a-40e. The process gas may comprise a mixture of the inert gas and the precursor monomer that is supplied by the process gas source 26 in a single stream or may comprise a combination that is delivered by the process gas source 26 through separate gas lines so that the mixture is only formed inside of the process chamber 14.

The process recipe for the polymerization process may be varied according to the nature of the plasma treatment. In one embodiment, the inert gas may comprise argon and the precursor monomer may comprise molecules of tetramethylcyclotetrasiloxane (TMCTS), hexamethyldisiloxane (HDMSO), or 1,1,3,3-tetramethyldisiloxane (tDMSO) in a gas or vapor. The molecules of the precursor monomer may be decomposed in the process of forming the plasma and the ionized molecules may combine (i.e., polymerize) as they condense on the interior surface 53. The plasma initiated reaction of monomer molecules may thereby form a coating or film 60 (FIG. 9) comprised of a polymer as chains and/or three-dimensional networks on the interior surface 53. In one embodiment, the polymer comprising the film 60 may be a siloxane.

Figure 3:
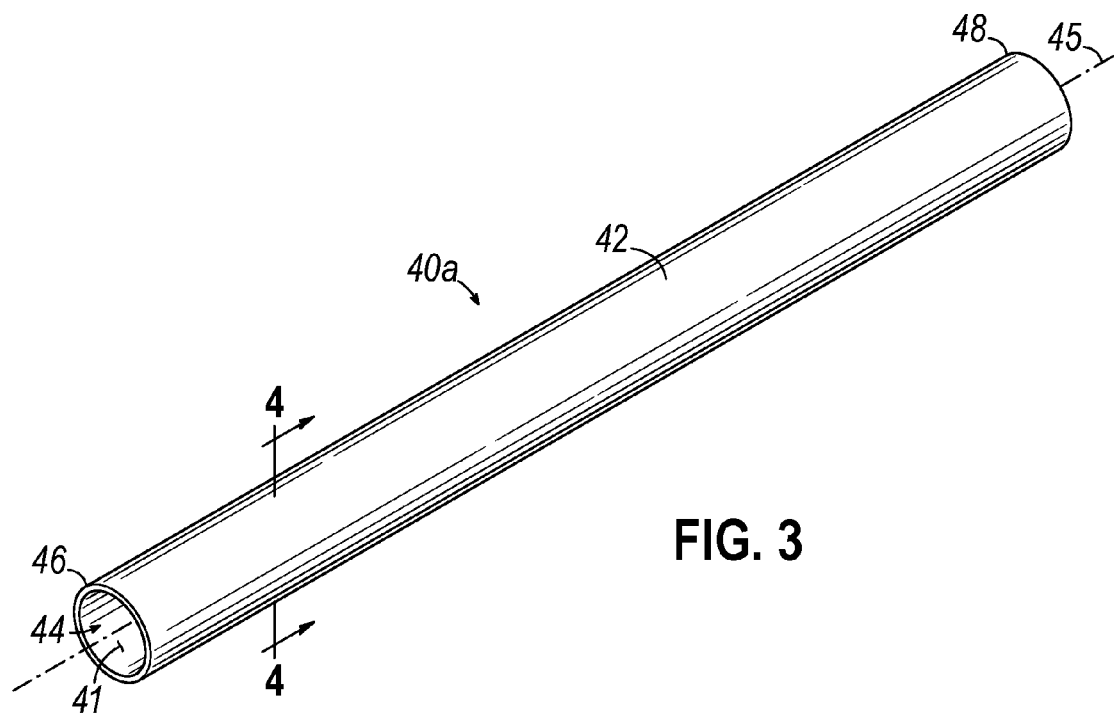
FIG. 3 is a perspective view of one of the conduits of FIG. 2.
Figure 4:
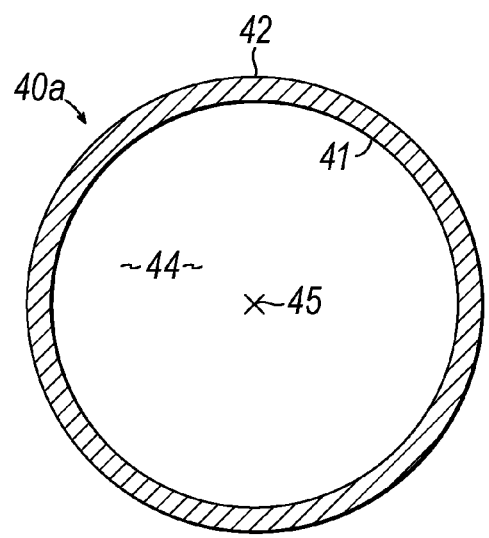
FIG. 4 is a cross-sectional view taken generally along line 4-4 in FIG. 3.

With reference to FIGS. 3 and 4 in which like reference numerals refer to like features in FIG. 2 and in accordance with an embodiment of the invention, each of the conductive conduits 40a-40e includes a sidewall 42 that surrounds a passage in the form of a lumen 44 extending along a longitudinal axis 45 from one end 46 to an opposite end 48. The lumen 44 is open at each of the ends 46, 48. In the representative embodiment, each of the conductive conduits 40a-40e comprises a hollow cylinder with an internal diameter and composed of an electrical conductor, such as a metal like an aluminum alloy.

Figure 5:
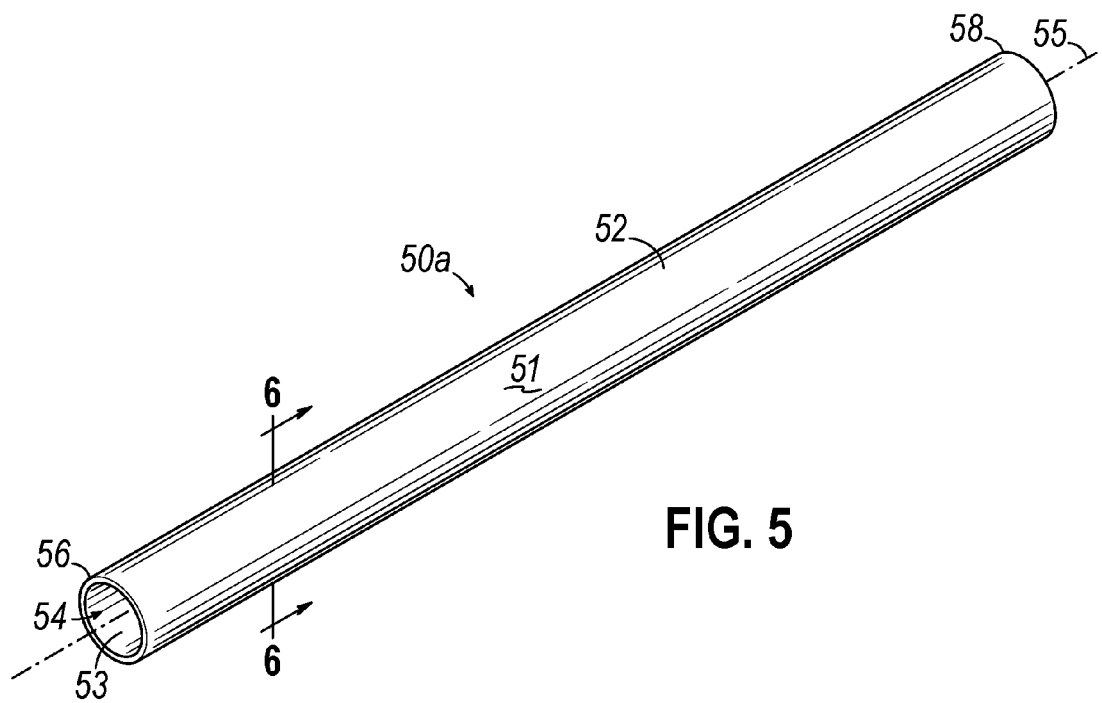
FIG. 5 is a perspective view of one of the tubes of FIG. 2.
Figure 6:
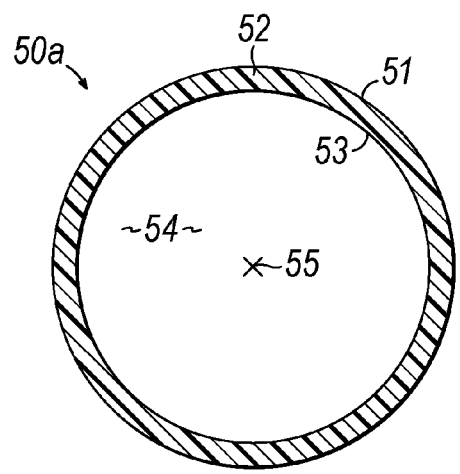
FIG. 6 is a cross-sectional view taken generally along line 6-6 in FIG. 5.

With reference to FIGS. 5 and 6 in which like reference numerals refer to like features in FIGS. 2-4, each of the tubes 50a-50e is lengthwise hollow and includes a sidewall 52 that surrounds a lumen 54 extending along a longitudinal axis 55 from one end 56 to an opposite end 58. The lumen 54 is open at each of the ends 56, 58. Because the conductive conduits 40a-40e are individually selected, there is no constraint on simultaneously processing tubes 50a-50e of different diameter tubes by using conductive conduits 40a-40e of different dimensions.

Figure 7:
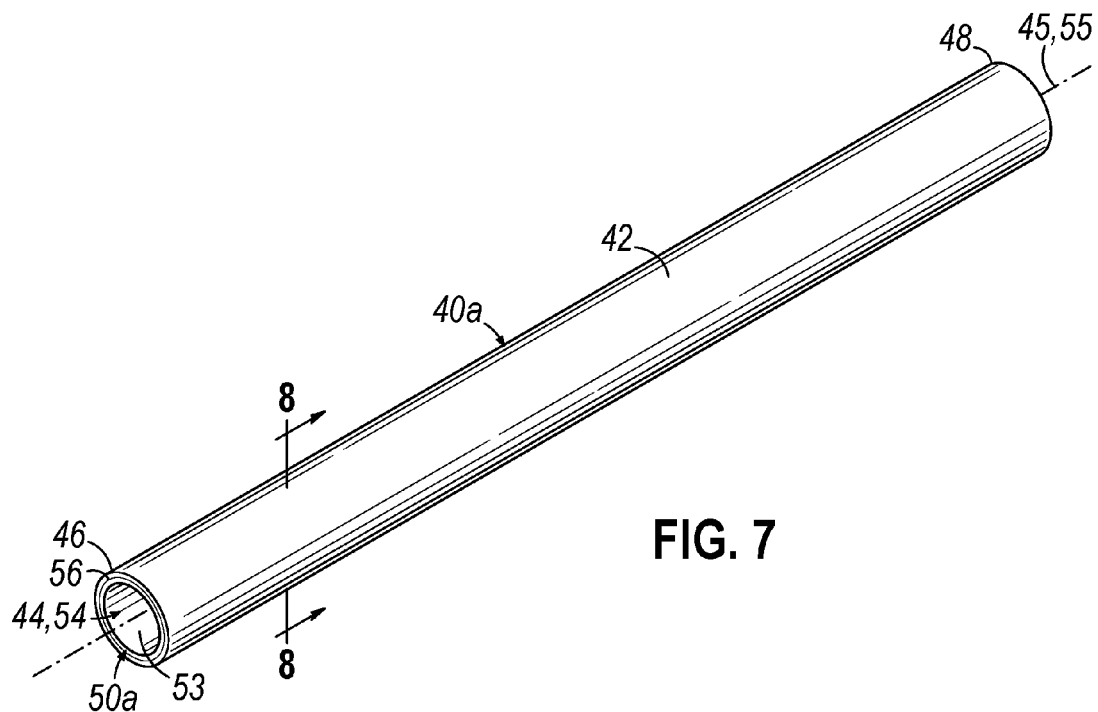
FIG. 7 is a perspective view of one of the tubes located inside one of the conduits.
Figures 8, 9:
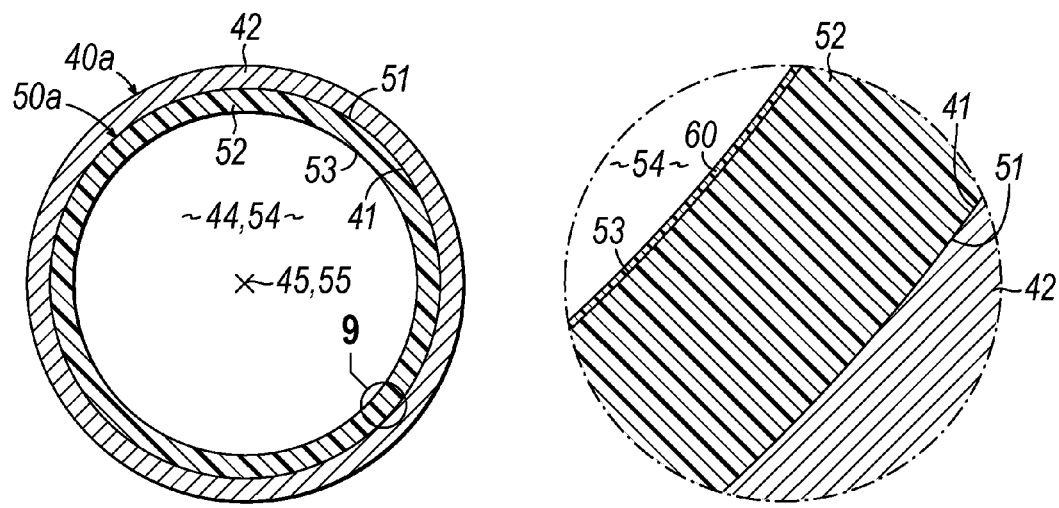
FIG. 8 is a cross-sectional view taken generally along line 8-8 in FIG. 7.
FIG. 9 is a detailed cross-sectional view of the encircled area of FIG. 8 after plasma treatment.

With reference to FIGS. 7-9 in which like reference numerals refer to like features in FIGS. 2-6 and in accordance with an embodiment of the invention, the tubes 50a-50e are placed inside of the conductive conduits 40a-40e and then batch processed with a plasma generated inside the process chamber 14 while the tubes 50a-50e reside inside of the conductive conduits 40a-40e. In one embodiment, one or both of the opposite ends 56, 58 of one or more of the tubes 50a-50e may be located inside the respective opposite ends 46, 48 of the corresponding one of the conductive conduits 40a-40e. In another embodiment, both of the opposite ends 56, 58 of each of the tubes 50a-50e may be located inside the respective opposite ends 46, 48 of the corresponding one of the conductive conduits 40a-40e.

The passages 44 of conductive conduits 40a-40e may be shape matched to the outer surface 51 of the tubes 50a-50e such that, when the tubes 50a-50e are inserted into the conductive conduits 40a-40e as best shown in FIGS. 7, 8, the clearance or gap between the outer surface 51 of the tubes 50a-50e and the interior surface 41 of the conductive conduits 40a-40e surrounding the passage 44 is minimized and, preferably, is negligible or non-existent. In particular, any gap may be small enough (e.g., less than or equal to 1 millimeter) so as to not support plasma excitation within the gap. If the lumen 44 of each of the conductive conduits 40a-40e has a cylindrical geometrical shape, then the outer diameter of the surface 51 and the inner diameter of the surface 41 may be configured to dimensionally match each other in order to minimize the gap. When the tubes 50a-50e are inserted into the conductive conduits 40a-40e, the longitudinal axes 45, 55 may be aligned so as to be parallel. In the representative embodiment, the longitudinal axes 45, 55 may be collinear because the respective pairs of tubes 50a-50e and conductive conduits 40a-40e are coaxial.

In a representative embodiment and as best shown in FIG. 2, the conductive conduits 40a-40e may be oriented in a parallel arrangement when resident on the shelf 28 such that their passages 44, 54 likewise have a parallel arrangement. For example, the passages 44 of the conductive conduits 40a-40e and, therefore, the passages 54 of the tubes 50a-50e may be oriented in a direction 39 of the process gas flow in the plasma treatment system 10. This orientation selection may increase the replenishment of process gas inside the passages 44 because of the preferential direction 39 of process gas flow parallel to longitudinal axes 45, 55 of the respective passages 44, 54. In particular, if the process gas flow in the plasma treatment system 10 is generally directed from the front of the process chamber 14 toward the rear of the process chamber 14, then the passages 44 of the conductive conduits 40a-40e may have the same orientation so that the process gas flow is directed from one end 46 to the opposite end 48.

The lumen 44 of each of the conductive conduits 40a-40e defines a structure analogous to a hollow cathode structure in which a high density plasma can be formed. However, the physics of plasma formation is contingent, among other things, upon providing an operating gas pressure that is optimized for plasma discharge. The process gas mixture and pressure may be optimized in order to reduce the intensity of the hollow cathode plasma generated inside the passages 44. This optimization may permit the plasma polymerization process to proceed without breaking down the monomer precursor and can thereby provide deposition inside the passages 54 and on the interior surface 53 of a coating or film 60 (FIG. 9) characterized by acceptable film quality. For example, the film 60 may have a uniform thickness at all locations on the interior surface 53 along the length along axis 55 between the opposite ends 56, 58 of the lumen 54.

In use, the process chamber 14 is vented to atmospheric pressure, the chamber door 18 is opened to expose the access opening, and each of the conductive conduits 40a-40e is populated with one of the tubes 50a-50e to provide the requisite pairings. The end 56 of each of the tubes 50a-50e is inserted into the lumen 44 of one of the conductive conduits 40a-40e at the one end 46. A force is then applied to move each of the tubes 50a-50e through the lumen 44 toward the opposite end 48 of the respective conductive conduit 40a-40e. The conductive conduits 40a-40e may be fixtures inside the process chamber 14 so that the tubes 50a-50e are placed inside conductive conduits 40a-40e with the conductive conduits 40a-40e at fixed locations. Alternatively, the tubes 50a-50e may be placed inside conductive conduits 40a-40e external to the process chamber 14 and the assemblies moved into the process chamber 14. When inside of the process chamber 14, the conductive conduits 40a-40e are coupled to the RF generator 30 so that the conduits 40a-40e can be part of the powered electrode.

The chamber door 18 is closed and the latch 20 is engaged to isolate the evacuable space 16 of the process chamber 14 from the ambient environment. The vacuum pumping system 23 is placed in communication with the evacuable space 16 using associated suitable valving, and atmospheric gases are evacuated from the evacuable space 16. Upon reaching an appropriate base pressure inside the process chamber 14, a flow of a process gas may be supplied to the evacuable space 16 from the process gas source 26 while the process chamber 14 is being evacuated by the vacuum pumping system 23. Specifically, the process gas source 26 supplies a process gas comprising an inert gas and a precursor monomer gas or vapor. The contribution of the partial pressure of the inert gas elevates the operating pressure inside the passages 54. A total pressure is established inside of the passages 54 of the tubes 50a-50e and, therefore, inside the passages 44 of conductive conduits 40a-40e that is sufficient to initiate and sustain a hollow cathode plasma within each set of pairs of passages 44, 54.

Once the desired process pressure is achieved and stabilized inside the process chamber 14, the RF generator 30 is energized to supply high-frequency electrical power to the conductive conduits 40a-40e, which excites the gas species comprising the process gas within the passages 54 to form a plasma. The conductive conduits 40a-40e are part of the powered electrode and are not merely floating objects in the plasma. The tubes 50a-50e are physically located between the process gas in the respective lumen 54 and the corresponding one of the conductive conduits 40a-40e. The molecules of the precursor monomer may be decomposed in the process of forming the plasma and the ionized molecules may combine (i.e., polymerize) as they condense on the interior surface 53. The plasma initiated reaction of the precursor monomer may thereby form the film 60 (FIG. 9) comprised of polymer chains and/or three-dimensional networks on the interior surface 53. If the precursor monomer comprises tetramethylcyclotetrasiloxane (TMCTS), hexamethyldisiloxane (HDMSO), or 1,1,3,3-tetramethyldisiloxane (tDMSO) in a gas or vapor, the film 60 may comprise a siloxane film.

In order to minimize depletion effects of the process gas within the tubes 50a-50e, to reduce heating, and to intraluminally grow a higher quality film 60, the RF power is pulsed during the deposition process so that the plasma is intermittently excited and extinguished for alternating successive time periods. The pulsing frequency and duty cycle are set such that fresh, unreacted gas species are able to diffuse from the evacuable space 16 into the tubes 50a-50e from the opposite ends 56, 58 between consecutive power pulses. For example, the pulsing parameters for film deposition may comprise a pulsing frequency of 1 Hz and a duty cycle of 10%. This particular combination of pulsing parameters translates to successive cycles in which 0.1 seconds of applied power to deposit the intraluminal coating followed by 0.9 seconds over which power application to the conductive conduits 40a-40e is absent so that the plasma is off and the passages 54 are replenished with unreacted precursor molecules. The selection of pulsing parameters may depend on the diameter and length (e.g., aspect ratio) of the tubes 50a-50e. Pulsing may also reduce the overall energy input to the conductive conduits 40a-40e, which may eliminate adverse heat degradation to the tubes 50a-50e.

During processing, the optimum deposition performance using a monomer precursor, such as TMCTS, may be achieved for process gas pressures less than or equal to 50 mTorr. Process gas pressures at, or below, this threshold pressure may improve the film quality of film 60 and/or prevent powder deposition. However, these process gas pressures for the monomer precursor are less than the gas pressure needed to generate a hollow cathode plasma within the lumen 44. For example, the process pressure needed to sustain a plasma inside the passages 54 may be greater than or equal to 75 mTorr.

These competing requirements for optimized deposition and the generation of a hollow cathode plasma may be reconciled with the introduction of a partial pressure of the inert gas to the process gas that includes a partial pressure of the monomer precursor. The partial pressure of the inert gas increases the overall process pressure (i.e., the sum of the partial pressures of the inert gas and the monomer precursor) to promote the generation of a hollow cathode plasma while keeping the partial pressure of the precursor monomer constant and at a level optimized for depositing a coating with high quality film properties. The partial pressure of the monomer precursor may be maintained at less than or equal to 50 mTorr and a partial pressure of the inert gas may be introduced to elevate the total pressure to a value greater than or equal to 75 mTorr.

The resultant deposition of the film 60 on the interior surface 53 of the lumen 54 of the tubes 50*a*-50*e* may be effective to modify or alter a property of the interior surface 53. For example, the film 60 may be effective for significantly reducing the tack of a high-friction material (e.g., rubber) tube while not providing an effect on the outer surface 51 of the tubes 50*a*-50*e*. For example, the tubes 50*a*-50*e* may be comprised of silicone rubber and the deposited film on the inner surface of the tubes 50*a*-50*e* may reduce the tack and the surface friction compared with the untreated condition. The processes of the various embodiments of the invention are relatively inexpensive and easy to implement for depositing tack-reduction films inside the tubes 50*a*-50*e*. The low tack surface may ease the insertion of objects or devices into lumen 54 of the tubes 50*a*-50*e*, as well as eliminate any undesired bonding between contacting silicone rubber surfaces over time.

In an alternative embodiment, the film 60 may comprise a different type of material and/or may have a different functionality. As examples, the film 60 may provide a diffusion barrier or may provide a chemically-active substance.

In an alternative embodiment, the tubes 50*a*-50*e* may be processed to provide the intraluminal coating without the use of the conductive conduits 40*a*-40*e* provided that the tubes 50*a*-50*e* are comprised of a conductor, such as a metal. The tubes 50*a*-50*e* comprise of a freestanding objects that form part of the powered electrode and are not merely floating objects in the plasma. An example of a freestanding object to which this use case is applicable is a stent, which only requires coupling of RF energy in a manner similar to that described hereinabove and with suitable process gas partial pressures and power control to initiate the intermittent hollow cathode plasma. Prior to processing, the stents may be coated with a tacky material, such as silicone, and then later attached to balloons for delivery. The film 60 may serve to prevent tacky material coating on the stent from adhering to the balloon at the time of device delivery in a patient.

EXAMPLE AND COMPARATIVE EXAMPLE

A silicone tubing was treated consistent with the embodiments of the invention. A sample of the silicon tubing was retained in an untreated condition as a control. The tubes were sliced in half longitudinally to create tubing specimens—one treated by application of the friction-reducing film and the other untreated.

The silicone tubing was placed inside of an aluminum conduit, which was in turn coupled with the power bus. The precursor monomer (tetramethylcyclotetrasiloxane (TMCTS)) was supplied to the process chamber at a volumetric flow rate of 3 standard cubic centimeters per minute (sccm) along with argon at a volumetric flow rate of 20 sccm. A siloxane film was deposited with a pressure in the process chamber at 120 mTorr, a power of 200 watts supplied to the conduit, a pulse frequency of 1 Hz, a pulse duty cycle of 10%, and a treatment time of 30 minutes.

The tubing specimens were subjected to linear reciprocating ball-on-flat wear testing. The test method involved sliding a spherically-ended specimen (or "ball" specimen against the flat inner surface of the two tubing specimens. The ball specimen and each tubing specimen were moved relative to one another in a linear, reciprocating sliding motion. A load was applied vertically downward through the ball specimen against the horizontally-mounted flat specimen. Because the test method involved reciprocating sliding where changes in the sliding velocity and direction of motion occur during the test, constant velocity conditions are not maintained. Dimensional changes for both ball specimen and each tubing specimen were used to calculate wear volumes and wear rates.

Friction forces were measured during the test and used to assess changes in the contact conditions or the kinetic friction coefficient as a function of time. The ball specimen was mounted on a stiff lever, designed as a frictionless force transducer. As the each tubing specimen was moved back and forth, resulting frictional forces acting between the ball specimen and the flat specimen were measured by very small deflections of the lever using an a linear variable differential transformer (LVDT) sensor. This testing method facilitates the determination and study of friction and wear behavior.

The test instrument was a Pin-on-Disk "Tribometer" commercially available from CSM Instruments. The test conditions and parameters were an applied normal force of 0.167 newtons, a stroke length of 50 millimeters, a sliding distance of 0.5 meters, and a maximum linear speed of 0.006 meters per second. Data was acquired for 5 cycles with the first cycle used for data analysis. The ball specimen had a diameter of 3 millimeters and was composed of SS 440C grade 25 stainless steel. The test was unlubricated, and was performed in air at room temperature.

Figure 10:
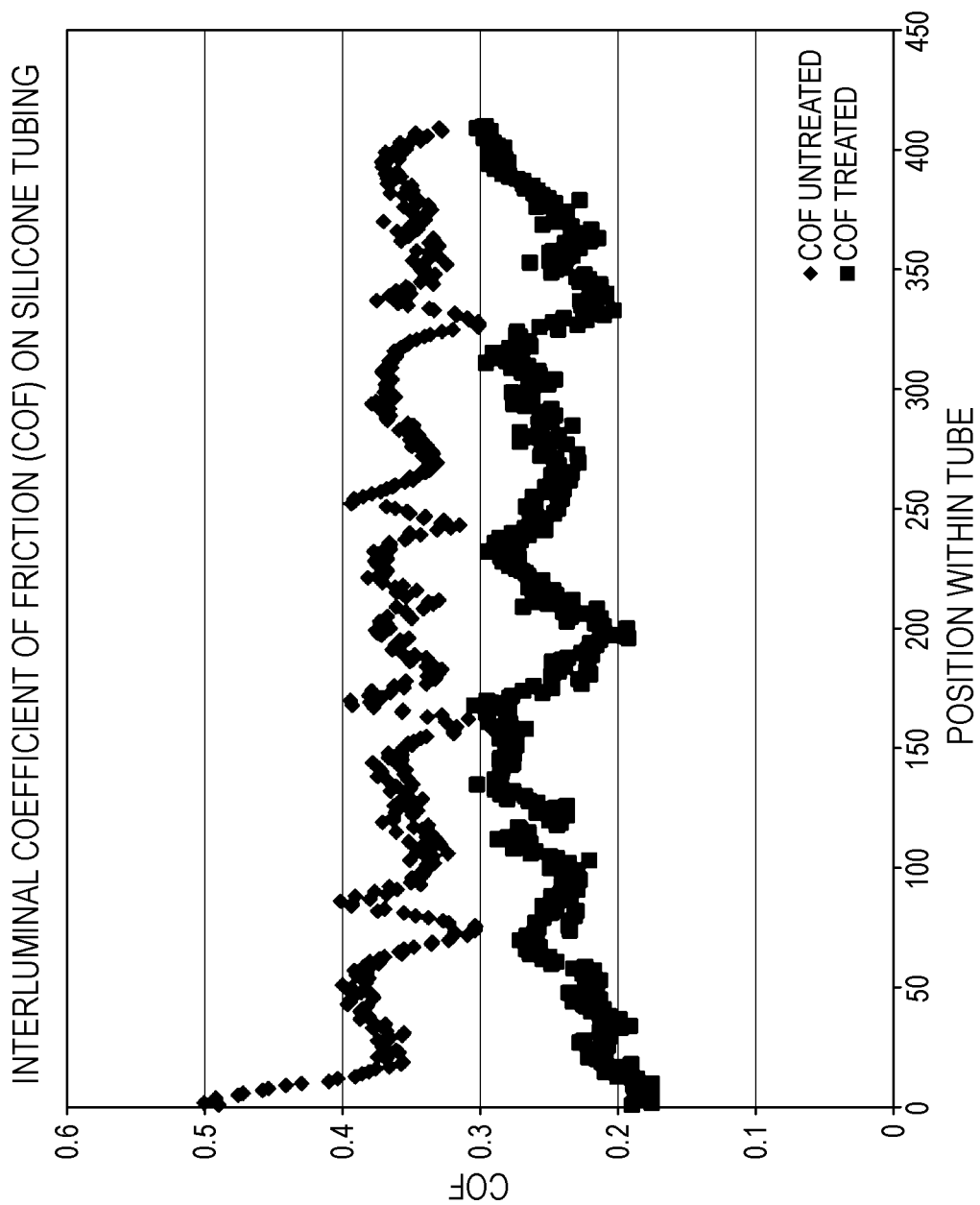
FIG. 10 is a graph showing the results of linear reciprocating ball-on-flat wear testing for an untreated specimen as a control and for a treated specimen to which a film has been applied in a manner consistent with the embodiments of the invention.

Measurements were performed along the interior surface of each tubing specimen in 5 segments of 50 millimeters each. When the data from the measurements was analyzed, the average coefficient of friction ($\mu$) as a function of the position of the ball specimen for the tubing specimens is plotted in FIG. 10. A 10-point moving average was applied for smoothing. The data for the treated specimen is represented in FIG. 10 by the lower set of data points, and the data for the untreated specimen is represented in FIG. 10 by the upper set of data points. The average coefficient of dynamic friction for the untreated tubing at all positions was determined to be 0.309±0.060, and the average coefficient of dynamic friction for the treated tubing at all positions was determined to be 0.246±0.114. As apparent from a comparison of the test results, the film coating the inner surface of the passage of the treated tubing was effective to reduce the average coefficient of dynamic friction.

References herein to terms such as "vertical", "horizontal", etc. are made by way of example, and not by way of limitation, to establish a frame of reference. It is understood various other frames of reference may be employed without departing from the spirit and scope of the invention.

It will be understood that when an element is described as being "connected" or "coupled" to or with another element, it can be directly connected or coupled to the other element or, instead, one or more intervening elements may be present. In contrast, when an element is described as being "directly connected" or "directly coupled" to or with another element, there are no intervening elements present. When an element is described as being "indirectly connected" or "indirectly coupled" to or with another element, there is at least one intervening element present.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicants' general inventive concept. The scope of the invention itself should only be defined by the appended claims.

What is claimed is:

1. A method of applying a coating to a plurality of articles, each article having a first end and a second end opposed to the first end, a passage, an interior surface surrounding the passage, and an exterior surface, the method comprising:
    placing the plurality of articles inside a plurality of conductive conduits, each conductive conduit having two opposing ends, a passage, and an interior surface that surrounds the passage such that, at least one of the first end and the second end of the each article is within the two opposing ends of one of the plurality of conductive conduits, and a gap is formed between the interior surface of each conductive conduit and the exterior surface of each respective article;
    generating a plasma discharge from a process gas inside the passage of each article when the article is inside the passage of one of the plurality of conductive conduits;
    preventing a plasma discharge in each gap between the interior surface of each conductive conduit and the exterior surface of each article; and
    depositing the coating from the plasma discharge on the interior surface of each of the plurality of articles.

2. The method of claim 1 wherein generating the plasma discharge inside the passage of each article comprises:
    supplying the process gas to the passage of each article at a total pressure within the passage including a partial pressure of an inert gas and a partial pressure of a precursor monomer.

3. The method of claim 2 wherein the precursor monomer is selected from the group consisting of tetramethylcyclotetrasiloxane, hexamethyldisiloxane, and 1,1,3,3-tetramethyldisiloxane (tDMSO).

4. The method of claim 2 wherein each conductive conduit is coupled with a power supply, and generating the plasma inside the passage of each article comprises:
    supplying radio frequency power from the power supply to each conductive conduit with a pulsing frequency and a duty cycle.

5. The method of claim 4 wherein the duty cycle includes power portions and non-powered portions, and the method further comprises replenishing the process gas within the passage of each article by inward gas flow from opposite ends of the article during non-powered portions of the duty cycle.

6. The method of claim 2 further comprising:
    elevating the total pressure of the process gas to support the plasma discharge inside the passage of each article by selecting the partial pressure of the inert gas.

7. The method of claim 2 further comprising: depositing the coating at a uniform thickness between first and second ends of each article by selecting the partial pressure of the precursor monomer.

8. The method of claim 7 further comprising:
    elevating the total pressure of the process gas to support the plasma discharge inside the passage of each article by selecting the partial pressure of the inert gas.

9. The method of claim 2 further comprising:
    orienting the passage of each conductive conduit and the passage of each article parallel to a direction of flow of the process gas inside a process chamber.

10. The method of claim 1, wherein the step of placing the plurality of articles inside of the plurality of conductive conduits comprises:
    placing one of the plurality of articles inside a respective one of the plurality of conductive conduits.

* * * * *